US009956365B2

(12) United States Patent
Bonassa et al.

(10) Patent No.: US 9,956,365 B2
(45) Date of Patent: May 1, 2018

(54) LUNG VENTILATION APPARATUS

(71) Applicant: CareFusion 2200, Inc., San Diego, CA (US)

(72) Inventors: Jorge Bonassa, São Paulo (BR); Adriano De Lima Santos, São Paulo (BR); José Augusto Calvo Lonardoni, Itapevi (BR)

(73) Assignee: VYAIRE MEDICAL CAPITAL LLC, Yorba Linda, CA (US)

( * ) Notice: Subject to any disclaimer, the term of this patent is extended or adjusted under 35 U.S.C. 154(b) by 756 days.

(21) Appl. No.: 14/251,548

(22) Filed: Apr. 11, 2014

(65) Prior Publication Data

US 2015/0290407 A1    Oct. 15, 2015

(51) Int. Cl.
*A61M 16/00* (2006.01)
*A61M 16/06* (2006.01)
(Continued)

(52) U.S. Cl.
CPC .... *A61M 16/0066* (2013.01); *A61M 16/0003* (2014.02); *A61M 16/0051* (2013.01); *A61M 16/024* (2017.08); *A61M 16/0666* (2013.01); *A61M 16/0833* (2014.02); *A61M 16/205* (2014.02); *G05B 15/02* (2013.01);
(Continued)

(58) Field of Classification Search
CPC .......... A61M 16/0066; A61M 16/0051; A61M 16/0666; A61M 16/0833; A61M 16/205; A61M 2016/003; A61M 2205/18; A61M 2205/3334; A61M 2205/35;
(Continued)

(56) References Cited

U.S. PATENT DOCUMENTS

| 4,773,411 A | 9/1988 | Downs |
| 5,107,830 A * | 4/1992 | Younes ................. A61M 16/00 128/204.18 |

(Continued)

FOREIGN PATENT DOCUMENTS

| WO | WO-2009039525 A2 | 3/2009 |
| WO | WO-2011089491 A1 | 7/2011 |

(Continued)

OTHER PUBLICATIONS

Laubscher et al. "An adaptive lung ventilation controller", 1994 IEEE, pp. 51-59.*

(Continued)

*Primary Examiner* — Van Nguyen
(74) *Attorney, Agent, or Firm* — McDermott Will & Emery LLP

(57) ABSTRACT

A lung ventilation apparatus and system are described. The lung ventilation apparatus may include a control panel; and a graphical user interface associated with the control panel, the graphical user interface comprising a central strip content item covering at least 50% of a total area of the graphical user interface, the central strip content item representing at least one of a patient monitoring screen or surveillance screen, the central strip content item comprising a first portion and a second portion, wherein the first portion comprises numerical elements indicating ventilation parameters of a patient, and the second portion comprises a graphical element indicating pressure at a patient airway.

19 Claims, 5 Drawing Sheets

(51) Int. Cl.
*A61M 16/08* (2006.01)
*A61M 16/20* (2006.01)
*G05B 15/02* (2006.01)
*G06F 19/00* (2018.01)

(52) U.S. Cl.
CPC ... *G06F 19/3406* (2013.01); *A61M 2016/003* (2013.01); *A61M 2205/18* (2013.01); *A61M 2205/3334* (2013.01); *A61M 2205/35* (2013.01); *A61M 2205/505* (2013.01); *A61M 2205/52* (2013.01); *A61M 2240/00* (2013.01); *G06F 19/3481* (2013.01)

(58) Field of Classification Search
CPC ........ A61M 2205/505; A61M 2205/52; A61M 2240/00; G06F 19/3481
See application file for complete search history.

(56) References Cited

U.S. PATENT DOCUMENTS

| | | | |
|---|---|---|---|
| 5,474,062 A | | 12/1995 | DeVires et al. |
| 5,582,163 A | | 12/1996 | Bonassa |
| 5,909,731 A | * | 6/1999 | O'Mahony ......... A61M 16/202 128/204.18 |
| 6,369,114 B1 | * | 4/2002 | Weil ........................ A61K 31/00 514/215 |
| 7,246,618 B2 | * | 7/2007 | Habashi ................. A61M 16/00 128/204.22 |
| 7,810,497 B2 | * | 10/2010 | Pittman ............. A61M 16/0051 128/204.18 |
| 8,186,344 B2 | * | 5/2012 | Bonassa ................. A61M 16/00 128/200.24 |
| 8,408,203 B2 | * | 4/2013 | Tham ................ A61M 16/0051 128/200.14 |
| 8,677,999 B2 | * | 3/2014 | Allum .................. A61M 16/04 128/202.27 |
| 8,876,728 B2 | * | 11/2014 | Baloa Welzien ........ A61B 5/08 600/533 |
| 2002/0043264 A1 | | 4/2002 | Wickham |
| 2005/0109340 A1 | | 5/2005 | Tehrani |
| 2006/0011195 A1 | | 1/2006 | Zarychta |
| 2007/0000494 A1 | * | 1/2007 | Banner ................ A61B 5/0205 128/204.23 |
| 2007/0199566 A1 | * | 8/2007 | Be'eri ............... A61M 16/0051 128/204.23 |
| 2008/0072902 A1 | | 3/2008 | Setzer et al. |
| 2008/0295839 A1 | | 12/2008 | Habashi |
| 2008/0295840 A1 | | 12/2008 | Glaw |
| 2010/0218766 A1 | | 9/2010 | Milne |
| 2011/0232644 A1 | | 9/2011 | Doyle |
| 2012/0024286 A1 | | 2/2012 | Boring |
| 2012/0179061 A1 | | 7/2012 | Ramanan et al. |
| 2012/0216811 A1 | * | 8/2012 | Kimm .................. A61M 16/00 128/204.23 |
| 2013/0074844 A1 | * | 3/2013 | Kimm ............... A61M 16/0051 128/204.23 |
| 2013/0125883 A1 | | 5/2013 | Bonassa et al. |
| 2015/0290408 A1 | | 10/2015 | Bonassa et al. |
| 2015/0290409 A1 | | 10/2015 | Bonassa et al. |

FOREIGN PATENT DOCUMENTS

| | | |
|---|---|---|
| WO | WO-2012085748 A1 | 6/2012 |
| WO | WO-2013175394 A1 | 11/2013 |

OTHER PUBLICATIONS

Borrello et al. "Modeling and Control of Systems for Critical Care Ventilation", 2005, pp. 2166-2180.*
Harris et al. "Continuous Monitoring of Lung Ventilation With Electrical Impedance Tomography", 1992 IEEE, pp. 1754-1755.*
Chen et al. "Comparisons between Circle and Structural Models in Lung Ventilation Reconstruction by Electrical Impedance Tomography", 2008 IEEE, pp. 53-57.*
Favre et al. "Closed-Loop Control of a Continuous Positive Airway Pressure Device", 2003 IEEE, pp. 419-422.*
International Search Report and Written Opinion for Application No. PCT/US2015/021589, dated Jun. 9, 2015, 11 pages.
International Search Report and Written Opinion for Application No. PCT/US2015/021590, dated May 29, 2015, 15 pages.
International Search Report and Written Opinion for Application No. PCT/US2015/021591, dated Jul. 1, 2015, 13 pages.

* cited by examiner

LUNG VENTILATION APPARATUS

TECHNICAL YIELD

The present disclosure generally relates to lung ventilation, and more particularly to a lung ventilation apparatus including a patient monitoring and surveillance graphical user interface configured to enhance patient surveillance and safety levels.

BACKGROUND

Patients requiring artificial ventilation are generally connected to lung ventilators that cyclically deliver volumes of a mixture of air and oxygen by means of positive pressure. Some lung ventilators may be designed to treat patients from neonates to adults, both in invasive and noninvasive ventilation configurations.

Nasal CPAP (Continuous Positive Airway Pressure) is a therapy for neonatal patients where the neonatal patient is non-invasively connected to a ventilator using a nasal prong and breaths spontaneously at a continuous positive airway pressure. Unlike invasive ventilation, it is not usual in this nasal CPAP scenario to monitor volume due to large leaks observed in the inspired volume by the patient. In contrast, the patient respiratory breathing presents a small fluctuation of pressure and, therefore, operators prefer to monitor the pressure in such a case.

SUMMARY

Aspects of the subject technology relate to an example lung ventilation apparatus comprising a graphical user interface arranged in a manner that promotes effective breathing monitoring and surveillance of a neonatal patient. In accordance with certain aspects, the example lung ventilation apparatus includes features that are seen to reduce cognitive load on the medical staff and enhance patient surveillance and safety aspects.

In accordance with certain aspects, an example lung ventilation apparatus may comprise a man-machine interface configured to facilitate and promote effective breathing monitoring and surveillance of a neonatal patient when caregiver is distant from the patient's bed.

In accordance with certain embodiments, an example man-machine interface may be configured to improve the visualization and recognition of the spontaneous breathing and apnea events during CPAP therapy, thereby enhancing patient safety Various aspects of the subject technology may be achieved, for example, by a lung ventilation apparatus comprising a graphical user interface associated with a control panel, the graphical user interface comprising a central strip covering at least 50% of its total area, the central strip representing a patient monitoring and surveillance screen, the central strip having at least two portions, namely, a first portion and a second portion, wherein the first portion comprises numerical elements indicating main ventilation parameters of the patient, and the second portion comprises a graphical element indicating pressure at the patient airway.

In certain embodiments, the first portion may present the numerical elements related to $FiO_2$, CPAP, and Respiratory Rate.

In certain embodiments, the graphical element that indicates pressure at the patient airway may be a floating element that moves proportionally to the pressure in a vertical way, in relation to a mark that indicates a CPAP adjusted level, in such configurations or implementations, the second portion may comprise two line marks showing pressure scale for minimum and maximum pressure fluctuation.

In certain embodiments, the pressure scale may automatically change to accommodate the mandatory cycles.

In certain embodiments, the floating element may comprise a color that indicates if the respiration cycle is in an inhalation or exhalation phase.

In other alternative embodiments, the graphical element that indicates pressure at the patient airway may be a rotating element that rotates proportionally to the pressure, in relation to a scale that indicates the adjusted level. The rotating element can be a pointer that moves in relation to a semicircular scale including CPAP adjusted level at a middle position. Also in such this case, the second portion may comprise two line marks showing pressure scale for minimum and maximum pressure fluctuation. In some examples, the pressure scale may automatically change to accommodate the mandatory cycles.

In certain examples, the rotating element may comprise a color that indicates if the respiration cycle is in an inhalation or exhalation phase In certain embodiments, the graphical user interface may comprises a third portion presenting an iconic element that indicates the occurrence of the respiratory cycle of the patient. For example, the iconic element may indicate the start, duration and completion of the inspiratory phase, the exhalation phase and the cycle type (e.g., spontaneous or backup). More specifically, the iconic element may represent the figure of the right and left lungs, the bronchial tree, the trachea and the diaphragm of the patient, in accordance with some embodiments. In certain embodiments, a color code may be used for the lungs to distinguish the inspiration and exhalation of the patient.

In certain embodiments, the first, second and third portions may be arranged in the central strip of the graphical user interface in a proportion of substantially ⅓ for each portion. For example, the first portion may be displayed at the right side of the patient monitoring screen. The second portion may be displayed at the left side of the patient monitoring screen. The third portion may be displayed between the first portion and the second portion, in accordance with some embodiments.

In certain embodiments, the graphical user interface may comprise a lower strip arranged to present alarm and control access menus arrayed in addition to fast access controls. For example, the lower strip covers a portion equivalent to substantially 15% of the total graphical user interface area.

In certain embodiments, the graphical user interface may also comprise an upper strip arranged to present general information, such as date, hour, patient type, etc., in addition to a middle section intended for visual alarm indicator. The upper strip may cover a portion having an area equivalent to substantially 5% of the total graphical user interface area, in accordance with some embodiments.

The subject technology is illustrated, for example, according to various aspects described below. Various examples of aspects of the subject technology are described as numbered clauses or embodiments (1, 2, 3, etc.) for convenience. These are provided as examples and do not limit the subject technology. It is noted that any of the dependent clauses may be combined in any combination with each other or one or more other independent clauses, to form an independent clause. The following is a non-limiting summary of some embodiments presented herein:

Clause 1. A lung ventilation apparatus comprising: a control panel, and a graphical user interface associated with the control panel, the graphical user interface comprising a central strip content item covering at least 50% of a total area of the graphical user interface, the central strip content item representing at least one of a patient monitoring screen or surveillance screen, the central strip content item comprising a first portion and a second portion, wherein the first portion comprises numerical elements indicating ventilation parameters of a patient, and the second portion comprises a graphical element indicating pressure at a patient airway.

Clause 2. The lung ventilation apparatus according to clause 1 or any of the other clauses, wherein the central strip content item covers 80% or more of the total area of the graphical user interface.

Clause 3. The lung ventilation apparatus according to clause 1 or any of the other clauses, wherein the graphical element that indicates pressure at the patient airway is a floating element that is configured to move proportionally to the pressure in a vertical way, in relation to a mark that indicates a Continuous Positive Airway Pressure (CPAP) adjusted level.

Clause 4. The lung ventilation apparatus according to clause 3 or any of the other clauses, wherein the floating element is a circle and the mark includes two arrows pointing inward and facing each other.

Clause 5. The lung ventilation apparatus according to clause 4 or any of the other clauses, wherein the second portion comprises two line marks showing pressure scale for minimum and maximum pressure fluctuation.

Clause 6. The lung ventilation apparatus according to clause 5 or any of the other clauses, wherein the pressure scale automatically changes to accommodate mandatory cycles.

Clause 7. The lung ventilation apparatus according to clause 3 or any of the other clauses, wherein the floating element comprises a color that indicates when the respiration cycle is in an inhalation or exhalation phase.

Clause 8. The lung ventilation apparatus according to clause 1 or any of the other clauses, wherein the graphical element that indicates pressure at the patient airway is a rotating element that is configured to rotates proportionally to the pressure, in relation to a scale that indicates the CPAP adjusted level.

Clause 9. The lung ventilation apparatus according to clause 8 or any of the other clauses, wherein the rotating element is a pointer that is configured to move in relation to a semi-circular scale including CPAP adjusted level at a middle position.

Clause 10. The lung ventilation apparatus according to clause 9 or any of the other clauses, wherein the second portion comprises two line marks showing pressure scale for minimum and maximum pressure fluctuation.

Clause 11. The lung ventilation apparatus according to clause 10 or any of the other clauses, wherein the pressure scale automatically changes to accommodate mandatory cycles.

Clause 12. The lung ventilation apparatus according to clause 8 or any of the other clauses, wherein the rotating element comprises a color that indicates when the respiration cycle is in an inhalation or exhalation phase.

Clause 13. The lung ventilation apparatus according to clause 1 or any of the other clauses, wherein the first portion presents numerical elements related to $FiO_2$, CPAP, and Respiratory Rate.

Clause 14. The lung ventilation apparatus according to clause 1 or any of the other clauses, wherein the graphical user interface comprises a third portion presenting an iconic element that indicates the occurrence of the respiratory cycle of the patient.

Clause 15. The lung ventilation apparatus according to clause 14 or any of the other clauses, wherein the iconic element indicates a start, duration, and completion of the inspiratory phase, the exhalation phase, and the cycle type.

Clause 16. The lung ventilation apparatus according to clause 14 or any of the other clauses, wherein the iconic element represents a figure of at least one of the right and left lungs, the bronchial tree, the trachea, or the diaphragm of the patient.

Clause 17. The lung ventilation apparatus according to clause 16 or any of the other clauses, wherein the iconic element represents the figure of the right and left lungs, and wherein a color code is used for the lungs to distinguish the inspiration and exhalation of the patient.

Clause 18. The lung ventilation apparatus according to clause 14 or any of the other clauses, wherein the first, second, and third portions are arranged in the central strip content item of the graphical user interface in a proportion of substantially ⅓ for each portion, the first portion being displayed at a right side of the patient monitoring screen, the second portion being displayed at a left side of the patient monitoring screen, and the third portion being displayed between the first portion and the second portion.

Clause 19. The lung ventilation apparatus according to clause 1 or any of the other clauses, wherein the graphical user interface comprises a lower strip content item arranged to present alarm and control access menus arrayed in addition to fast access controls, the lower strip content item covering a portion equivalent to substantially 15% or more of the total graphical user interface area.

Clause 20. The lung ventilation apparatus according to clause 1 or any of the other clauses, wherein the graphical user interface comprises an upper strip content item arranged to present general information including at least one of a date, hour, or patient type, in addition to a middle section configured to provide a visual alarm indicator, the upper strip content item covering a portion including an area equivalent to substantially 5% or more of the total graphical user interface area.

Clause 21. A system for lung ventilation, the system comprising: a graphical user interface; one or more processors and a memory including instructions that, when executed by the one or more processors, cause the one or more processors to: generate, on the graphical user interface, a central strip content item covering at least 50% of a total area of the graphical user interface, the central strip content item representing at least one of a patient monitoring screen or surveillance screen, the central strip content item comprising a first portion and a second portion, wherein the first portion comprises numerical elements indicating ventilation parameters of a patient, and the second portion comprises a graphical element indicating pressure at a patient airway.

Clause 22. A machine-readable medium comprising instructions stored therein, which when executed by a machine, cause the machine to perform operations, the machine-readable medium comprising: instructions for generating, on a graphical user interface, a central strip content item covering at least 50% of a total area of the graphical user interface, the central strip content item representing at least one of a patient monitoring screen or surveillance screen, the central strip content item comprising a first portion and a second portion, wherein the first portion comprises numerical elements indicating ventilation parameters of a patient, and the second portion comprises a graphical element indicating pressure at a patient airway.

It is understood that various configurations oldie subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
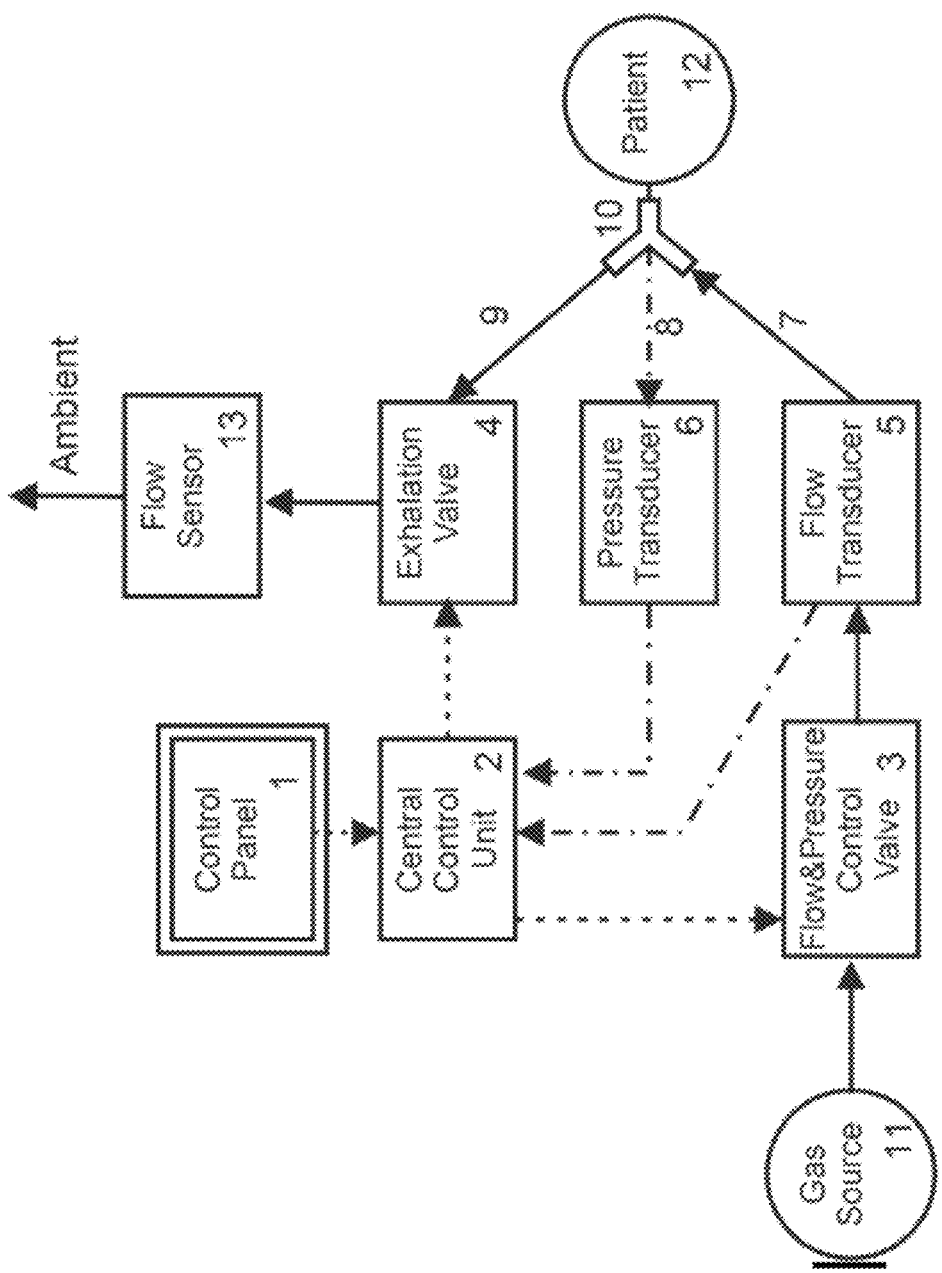
FIG. 1 is a schematic representation of an example of a mechanical lung ventilation system including a lung ventilation apparatus, a respiratory circuit, and a patient, in accordance with aspects of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Initially, several example lung ventilation devices will be described to compare and contrast other aspects of the present disclosure. For example, although some lung ventilation devices having may be designed specifically for infant nasal CPAP therapy, the use of some full range ventilators is seen as widespread for a number of reasons. For example, certain full range ventilators may have more flexibility to change between modes, backup ventilation in case of patient apnea, higher accuracy in controls, monitors and alarms, better monitoring capabilities, mainly larger screens to monitor patient data as well as trending and communication capabilities.

However, the alarms and monitors associated to flow and volume measurements can typically be ineffective in the specific application of infant CPAP therapy. In such a case, a main monitored parameter may be the airway pressure besides an inspired fraction of oxygen $FiO_2$ and respiratory rate. In addition, the pressure x time plot may be the main graph available to monitor the respiratory interaction of the patient with the ventilator device, for example.

In certain situations, traditional pressure×time plots may not be effective in showing patient breathing in relation to the CPAP level. For example, the pressure fluctuation can be less than 0.5 $cmH_2O$ in as CPAP level of 5 or more, making the view of this plot is difficult from distance, requiring the caregiver to be closer to the ventilator to examine if the patient is breathing adequately. It is pertinent to note that continuous inspection of patient breathing as well as pulse oximetry and cardiac rhythm are typically basic monitoring recommended for neonates during CPAP therapy.

Some lung ventilation devices may attempt to decrease cognitive load and focus on relevant information on a patient vigilance screen. In such implementations, volume measurements as well as pressure and rate may constitute the basic information arranged to promote perception of patient conditions even at some distance from the lung ventilation device.

In view of the above examples, an example lung ventilation apparatus and system of FIG. 1 and example arrangements of information on a graphical user interface illustrated in FIGS. 2-4 will be described. The example lung ventilation apparatus and system may be configured to provide enhancements in a ventilator graphical user interface with regard to infant nasal CPAP therapy. For example, aspects of the present disclosure may enable optimization of spontaneous breathing monitoring and capability for eventual apnea detection. In this regard, the example lung ventilation apparatus can be arranged in a manner to facilitate the monitoring of neonates spontaneous breathing during CPAP mode, whereby the patient spontaneous respiration is presented in a way that allows easy visualization and interpretation at distance. Accordingly, the cognitive load on the medical staff may be reduced, and patient surveillance and safety may be enhanced.

FIG. 1 schematically represents an example ventilation system related to the present disclosure, comprising a flow and pressure control valve 3 coupled to a gas source 11, usually an air and oxygen mixture from blender valve from outside or inside the ventilator, which controls the inspiratory flow by means of an inflow tube 7 coupled to a patient 12 by a "Y" shaped connector 10. The patient 12 exhales the gas through an outflow tube 9, coupled to the other end of the "Y" shaped connector 10, as controlled by the exhalation valve 4. The airway pressure of the patient is transmitted from the "Y" shaped connector 10, which is coupled to a pressure transducer 6 by a tube 8.

The inspiratory flow can be measured by a flow transducer 5 positioned downstream from the flow and pressure control valve 3. Both inspiratory flow and airway pressure signals coming from the flow transducer 5 and pressure transducer 6, together with the parameters adjusted in the control panel 1, may be used by a central control unit 2 to servo control the flow and pressure valves 3 and the exhalation valve 4, that, in general, is coupled to a flow sensor 13 which measures exhaled flow and volume.

Specifically during application of CPAP therapy, a constant flow, as set/adjusted by an operator, may be delivered by the flow and pressure control valve 3 through the inflow tube 7 to a nasal prong at the "Y" shape connector 10, and to the exhalation valve 4 through the outflow tube 9. The exhalation valve 4 can be servo controlled to maintain the measured pressure dose to patient nares at prong constant, as set/adjusted by user.

Although an example configuration of a ventilation system is shown in detail in FIG. 1, the subject technology is not limited to this specific arrangement, encompassing various alternatives that are used in the field, in addition to future equivalent embodiments.

During certain implementations of CPAP therapy, patient breaths spontaneously from the flow of delivered gas to the inflow tube 7 of respiratory circuit. Flow may be adjusted at 6 to 10 L/min, for example, which is enough to meet neonates' respiratory demand and compensate for possible leaks, and pressure may be set/adjusted around 3 to 5 $cmH_2O$, rarely more than 8 $cmH_2O$.

During inspiration, a portion of continuous flow may be diverted from the circuit to the patient lungs due to inspiratory effort, causing a small drop in the airway pressure, close to the patient's nares. In general, the pressure drop observed during inspiration can be used to detect patient breathing: the pressure drop is compared to a sensitivity level set/adjusted by the user and detects the inspiration whenever the pressure reaches the sensitivity threshold.

During exhalation, part of the inspired gas simply leaks and part exhales through outflow tube 9 to the exhalation valve, thus causing a small pressure increase in the airway. Due to the closed loop control, continuous flow and leaks, these pressure fluctuations are very small, for example, less than 1 $cmH_2O$ in relation to CPAP level.

It is also possible, during CPAP therapy, to set/adjust a BACKUP RATE as a safety feature. Whenever the example ventilator detects that the patient is apneic for a period longer than set/adjusted by the user in the control panel, the ventilator will deliver respiratory cycles by applying a positive pressure above CPAP level to promote lung expansion and alveolar ventilation and oxygenation. In certain embodiments, all parameters for BACK UP are pre-configured by the user.

According to the present disclosure, the lung ventilation apparatus may comprise a graphical user interface, associated to a control panel, by which one or more of the following steps can be taken (not necessarily in the order below):

Adjustment of the control parameters: CPAP, Backup Rate, Backup Inspiratory Pressure, Apnea Interval Limit, Sensitivity, among others;
Monitoring of respiratory curves;
Digital monitoring of several parameters such as pressure, frequency, among others;
Adjustment and audible/visual signalization of the alarms;
Adjustment of service routines and configuration;
Monitoring trend data, alarm records, events, etc.; and
Controlling and monitoring of specific maneuvers during mechanical ventilation.

The various functions can be organized and/or grouped in specific screens, accessible directly or by menus.

According to certain embodiments the graphical user interface is provided with at least a processing unit (e.g., a microprocessor or microcontroller) that can be independent from the processing unit responsible to control of the mechanical ventilation, whereby a fault in the interface does not affect the operation of the ventilator and vice-versa. All the safety requirements may be defined by applicable standards as well as risk analysis guiding the best construction options, for example.

Still according to a certain implementations, the graphical user interface may include a touch screen, in addition to a rotating or sliding control button, or some other technology performing equivalent adjustment functions that complies with the required purposes.

Figure 2:
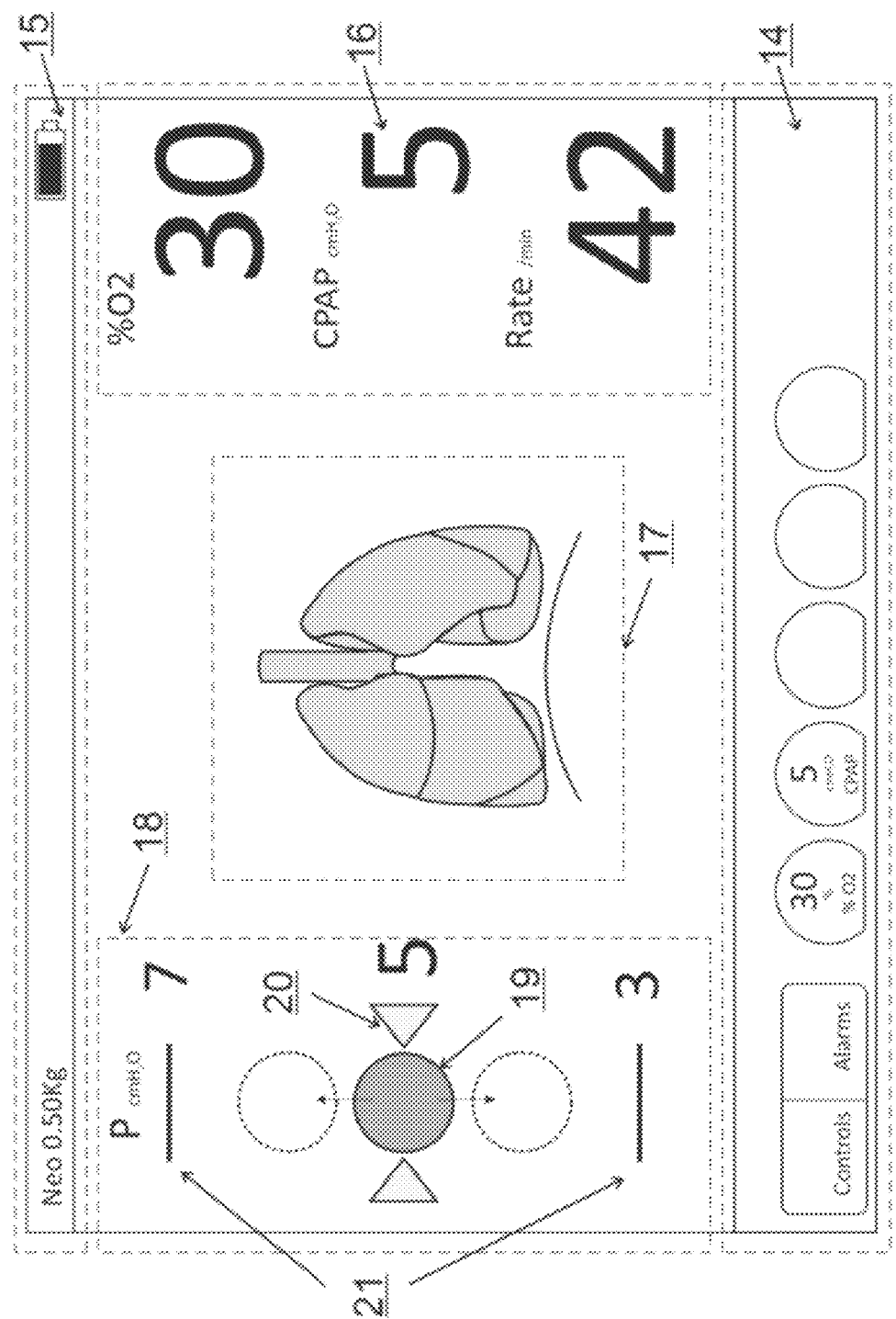
FIG. 2 illustrates an example of an arrangement of a graphical user interface of the lung ventilation apparatus, in accordance with aspects of the present disclosure.

The graphical user interface may be provided with a patient monitoring and surveillance screen, represented in FIG. 2, which displays details of the elements according to various aspects to the present disclosure.

As presented in the example of FIG. 2, the patient monitoring and surveillance screen may cover most of the graphical user interface area, for example, the central part, with the adjacent areas available for access and control functions, as well as other indications such as date, time, battery level, etc.

In accordance with certain embodiments of the present disclosure, on the lower strip of the graphical user interface 14, the alarm and control access menus are arrayed in addition to fast access controls, covering a portion equivalent to substantially 15% of the total graphical user interface area. The upper strip of the graphical user interface 15 may cover a portion having an area equivalent to substantially 5% of the total graphical user interface area, and it is arranged to present general information, such as date, hour, patient type, etc., in addition to a middle section intended for visual alarm indicator. The size of these adjacent areas (upper and lower portions 14, 15) is arranged and configured to be sufficient to display the necessary elements, allowing its viewing at short distances.

The remaining of the display, which consists in the central strip 16, 18, 17 of the graphical user interface, may cover substantially 80% of the total graphical user interface area and it is arranged to present the patient monitoring and surveillance screen, including elements to be viewed from a further distance, such as distance greater than 3 meters. Due to the dimensions and proportions of the graphical display, its visualization may be increased proportionally. According to certain aspects, the central strip 16, 18, 17 may cover at least substantially 50% of the total graphical user interface area in order to provide a satisfactory visualization by the operator.

More specifically, the central strip 16, 18, 17 of the graphical user interface may comprise three portions, for example: a first portion 16, a second portion 18, and a third portion 17. These three portions are intended respectively for the presentation of one or more of the following: (i) numerical elements indicating the main ventilation parameters of the patient (e.g., first portion 16); (ii) a graphical element indicating pressure at the patient airway (e.g., second portion 18); and (iii) an iconic element indicating the occurrence of the respiratory cycle of the patient (e.g., third portion 17).

The above elements are seen to be sufficient to characterize the mechanical ventilation status, allowing the operator to watch the patient at distance with no need for interpretation, as he/she can be alerted by simply viewing each element.

In certain embodiments, the three portions of central strip 16, 17 cover almost the same area, with approximately one third (⅓) assigned to each portion. In accordance with certain embodiments, these portions may be divided vertically, as illustrated in the example of FIG. 2, although, it is to be appreciated that this proportionality and the array may differ depending on the application and implementation of the subject technology.

The configuration and proportionality of the above mentioned portions 16, 18, 17 were specifically designed for use in certain embodiments and implementations to promote a reduction of the cognitive load of the medical staff members with regard to patient surveillance and monitoring, mainly in order to allow immediate visualization of all the critical aspects of the patient by the staff members at the medical post that is located away from the beds.

Particularly, for somec embodiments of the present disclosure, a 12" display was considered and implemented. However, it is to be appreciated that other sizes of display may be implemented in accordance with aspects of the present disclosure.

Furthermore, according to aspects of the present disclosure, first portion 16 can be displayed on the right side of the patient monitoring screen, presenting the numerical elements related to % $O_2$ (Fi$O_2$), CPAP, and Respiratory Rate. It should be noted that adequately-sized fonts must be used as required for visualization at distance. For one example embodiment, Calibri 100 font was used in the 12" display. Alternatively, other types of font may be also used.

On the left of the remaining area of the graphical user interface, as illustrated in the example of FIG. 2, second portion 18 presents a graphic element intended to indicate neonate's breathing.

In certain embodiments, the pressure fluctuations measured at airway, close to the prong, may be indicated by a floating element that moves proportionally to the pressure in a vertical way, in relation to a mark that indicates the CPAP adjusted level. In certain embodiments, the floating element is a circle 19 and the mark 20 consist in two arrows pointing inward, facing each other. Also, there may be two line marks 21 showing pressure scale for minimum and maximum pressure fluctuation. These limits can be set/adjusted by operator or automatically set/adjusted based on pressure fluctuations measurements. As expected, fluctuation is around ±1 cm$H_2O$, maximum and minimum pressure limits of ±2 in relation to CPAP level, for example, will give proper fluctuation amplitude to be visualized by any operator located away from the ventilator.

Also, in certain embodiments, when back-up ventilation is enabled and the ventilator delivers a positive pressure mandatory cycle whenever patient's apnea is detected, the pressure scale automatically changes to accommodate the mandatory cycles as inspiratory pressures are usually above spontaneous breathing range during backup mandatory breaths.

In certain embodiments, alongside a circular element movement associated with breathing, a color code may also be used to distinguish the inspiration and exhalation of the neonate. In certain configurations, during the exhalation phase of the respiratory cycle, the color of the circle is grey (#666666). When patient starts inhaling, the circle area color may change throughout all inspiration, depending on the type of respiratory cycle, as follows:
  orange (#FF9900)—back-up mandatory inspiratory cycle; and
  green (#00FF00)—spontaneous inspiratory cycle.

At the start of exhalation, the circle's color may returns to expiratory status.

The use of this visual element with proper amplification of neonate's shallow spontaneous breathing, give the caregiver the necessary monitoring tool to facilitate patient's vigilance.

Additionally, in order to improve the quality of pressure signal, a digital or analog signal filter may be used to separate breathing activity from any noise, as flow oscillations, rainout in the circuit, etc.

Figure 3:
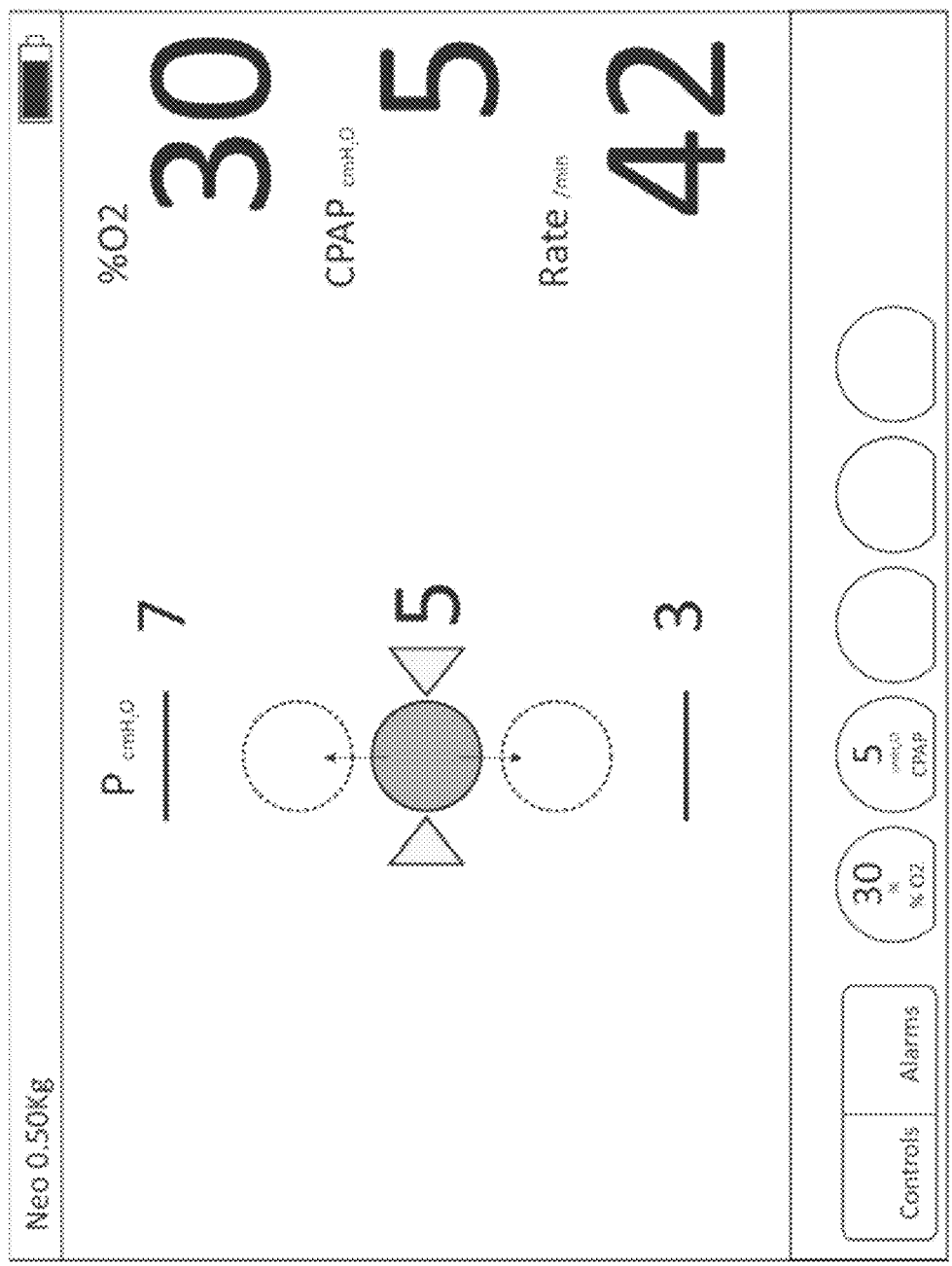
FIG. 3 illustrates an example of a graphical representation of another arrangement of the graphical user interface of the lung ventilation apparatus, in accordance with aspects of the present disclosure.

In certain embodiments, the floating circle element can be used alone (e.g., without the third portion 17) in order to decrease cognitive load, as indicated in the example of FIG. 3. This configuration results in a minimalist vigilance screen compatible with CPAP therapy safety requirements.

Figure 4:
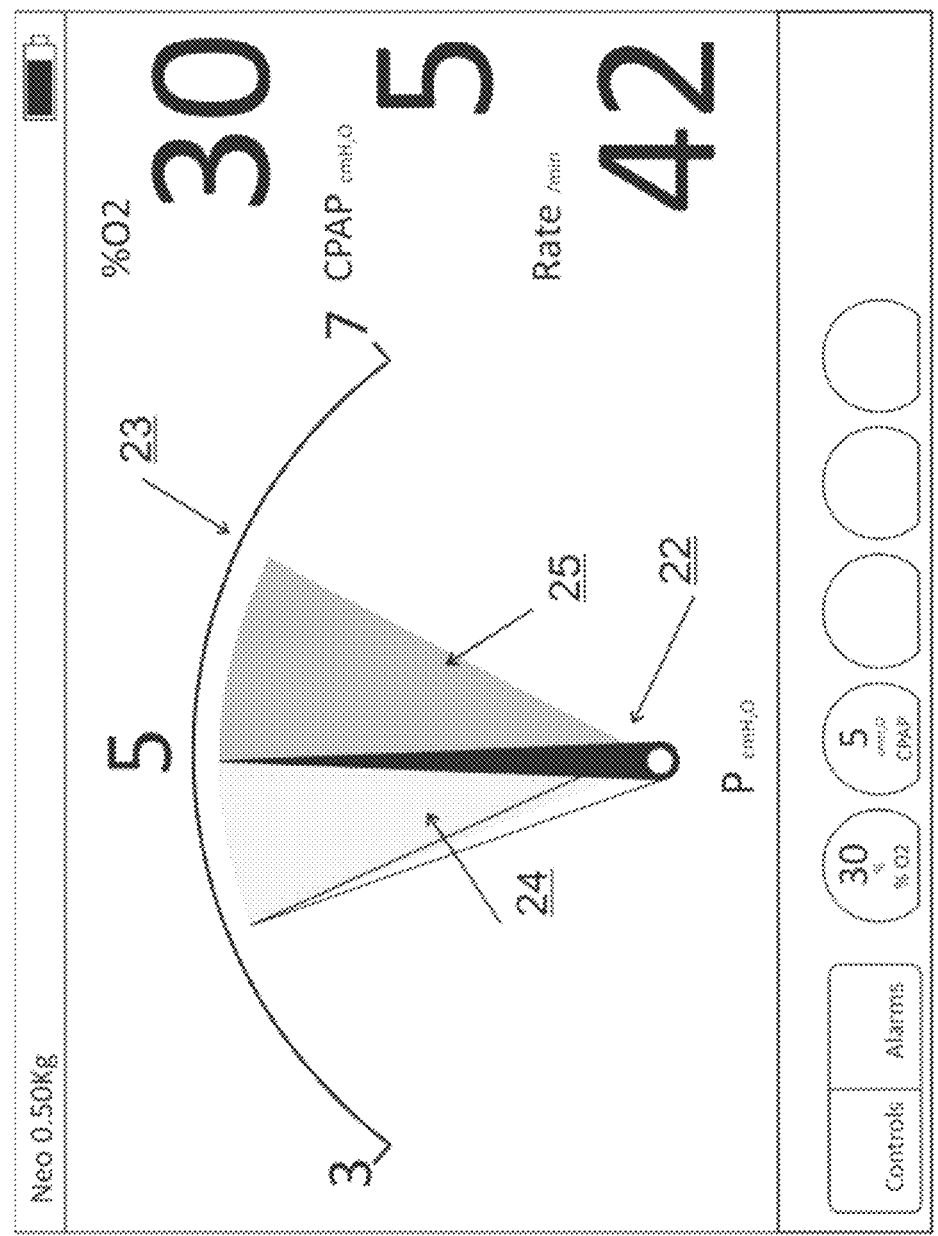
FIG. 4 illustrates an example of a graphical representation of another arrangement of the graphical user interface of the lung ventilation apparatus, in accordance with aspects of the present disclosure.

In other embodiments, the pressure fluctuations measured at airway, close to the prong, may be indicated by an element that rotates proportionally to the pressure in relation to a scale that indicates the CPAP adjusted level, as can be seen in FIG. 4. In this case, for example, the rotating element is a pointer 22 that moves in relation to a semi-circular scale 23 including CPAP level at a middle (12:00 hours) position as well as inspiratory and expiratory pressure fluctuations. Also, there are two line marks showing pressure scale for minimum and maximum pressure fluctuation. These limits can be set/adjusted by the operator or automatically set/adjusted based on pressure fluctuations measurements. As expected, fluctuation is around ±1 cm$H_2O$, maximum and minimum pressure limits of ±2 in relation to CPAP level, for example, will give proper fluctuation amplitude to be visualized by an operator located away from ventilator.

Also, in certain embodiments, alongside pointer movement associated with breathing, a color code may also be used to distinguish the inspiration and exhalation of the neonate. In certain configurations of these embodiments, during the exhalation phase of the respiratory cycle, the area 25 covered by the pointer is grey (#666666). When patient starts inhaling, the area 24 color defined by the pointer from CPAP level to the minimum pressure may change throughout all inspiration, depending on the type of respiratory cycle, as follows:
  orange (#FF9900)—back-up mandatory inspiratory cycle; and
  green (#00FF00)—spontaneous inspiratory cycle.

Finally, the third portion 17 in the example of FIG. 2 may present an iconic element that is intended to identify the respiratory cycle, specifically the start, duration and completion of the inspiratory phase, the exhalation phase and the cycle type (spontaneous or backup).

Particularly, in certain configurations, the iconic element represents the figure of the right, and left lungs, the bronchial tree, the trachea and the diaphragm. In order to clearly show the patient breathing rhythm, a color code is used for the lungs to distinguish the inspiration and exhalation of the neonate. In certain configurations, during the exhalation phase of the respiratory cycle, the color of the lung is grey (#666666). When patient starts inhaling, the area color may change throughout all inspiration, depending on the type of respiratory cycle, as follows:
  orange (#FF9900)—backup inspiratory cycle; and
  green (#00FF00)—spontaneous inspiratory cycle.

At the end of inspiration, the lung color may return to expiratory status.

The color change is easily noticed from some distance away, even at high breathing rates, as is in the case with neonatal patients. Particularly in these cases, where respiratory cycles are brief and volumes are small, the color code is the most effective resource for identifying the occurrence of an event.

As mentioned earlier, the pressure fluctuations during spontaneous breathing may not be detectable enough to give a reliable reading of inspiration and exhalation. The lung ventilator may use other means to detect patients breathing more precisely. The measurement of both of inspiratory flow and exhaled flow by transducers of the ventilator can be used to identify breathing pattern and distinguish patient inspiration and exhalation. Another alternative would be the use of specific sensors to detect patient's chest expansion, or still, other sensors of state of art, as heated wires and pneumotachs, only to mention some examples.

According to the above disclosed embodiments, the visualization and vigilance of neonate's breathing, during CPAP therapy are improved, reducing cognitive load and associated risks.

In accordance with various aspects of the subject technology, an example lung ventilation apparatus may be provided with a graphical user interface associated with a control panel. The graphical user interface comprising a central strip covering at least 50% of its total area, the central strip representing a patient monitoring and surveillance screen, the central strip having at least two portions, namely, a first portion and a second portion, wherein the first portion comprises numerical elements indicating the main ventilation parameters of the patient, and the second portion comprises a graphical element indicating pressure at the patient airway.

In some aspects, the central strip covers substantially 80% of the total area of the graphical user interface.

In some aspects, the graphical element that indicates pressure at the patient airway is a floating element that moves proportionally to the pressure in a vertical way, in relation to a mark that indicates a CPAP (Continuous Positive Airway Pressure) adjusted level.

In some aspects, the floating element is a circle and the mark consists in two arrows pointing inward, facing each other.

In some aspects, the second portion comprises two line marks showing pressure scale for minimum and maximum pressure fluctuation.

In some aspects, the pressure scale automatically changes to accommodate the mandatory cycles.

In some aspects, the floating element comprises a color that indicates if the respiration cycle is in an inhalation or exhalation phase.

In some aspects, the graphical element that indicates pressure at the patient airway may be a rotating element that rotates proportionally to the pressure, in relation to a scale that indicates the CPAP (Continuous Positive Airway Pressure) adjusted level.

In some aspects, the rotating element is a pointer that moves in relation to a semi-circular scale including CPAP adjusted level at a middle position.

In some aspects, the second portion comprises two line marks showing pressure scale for minimum and maximum pressure fluctuation.

In some aspects, the pressure scale automatically changes to accommodate the mandatory cycles.

In some aspects, the rotating element comprises a color that indicates if the respiration cycle is in an inhalation or exhalation phase.

In some aspects, the first portion may present the numerical elements related to CPAP and Respiratory Rate.

In some aspects, the graphical user interface may comprise a third portion presenting an iconic element that indicates the occurrence of the respiratory cycle of the patient.

In some aspects, the iconic element may indicate the start, duration and completion of the inspiratory phase, the exhalation phase and the cycle type (spontaneous or backup).

In some aspects, the iconic element may represent the figure of the right and left lungs, the bronchial tree, the trachea and the diaphragm of the patient.

In some aspects, a color code may be used for the lungs to distinguish the inspiration and exhalation of the patient.

In some aspects, the first, second and third portions may be arranged in the central strip of the graphical user interface in a proportion of substantially ⅓ for each portion, the first portion being displayed at the right side of the patient monitoring screen, the second portion being displayed at the left side of the patient monitoring screen, and the third portion being displayed between the first portion and the second portion.

In some aspects, the graphical user interface may comprise a lower strip arranged to present alarm and control access menus arrayed in addition to fast access controls, the lower strip covering a portion equivalent to substantially 15% of the total graphical user interface area.

In some aspects, the graphical user interface comprises an upper strip arranged to present general information, such as date, hour, patient type etc., in addition to a middle section intended for visual alarm indicator, the upper strip covering a portion having an area equivalent to substantially 5% of the total graphical user interface area.

Figure 5:
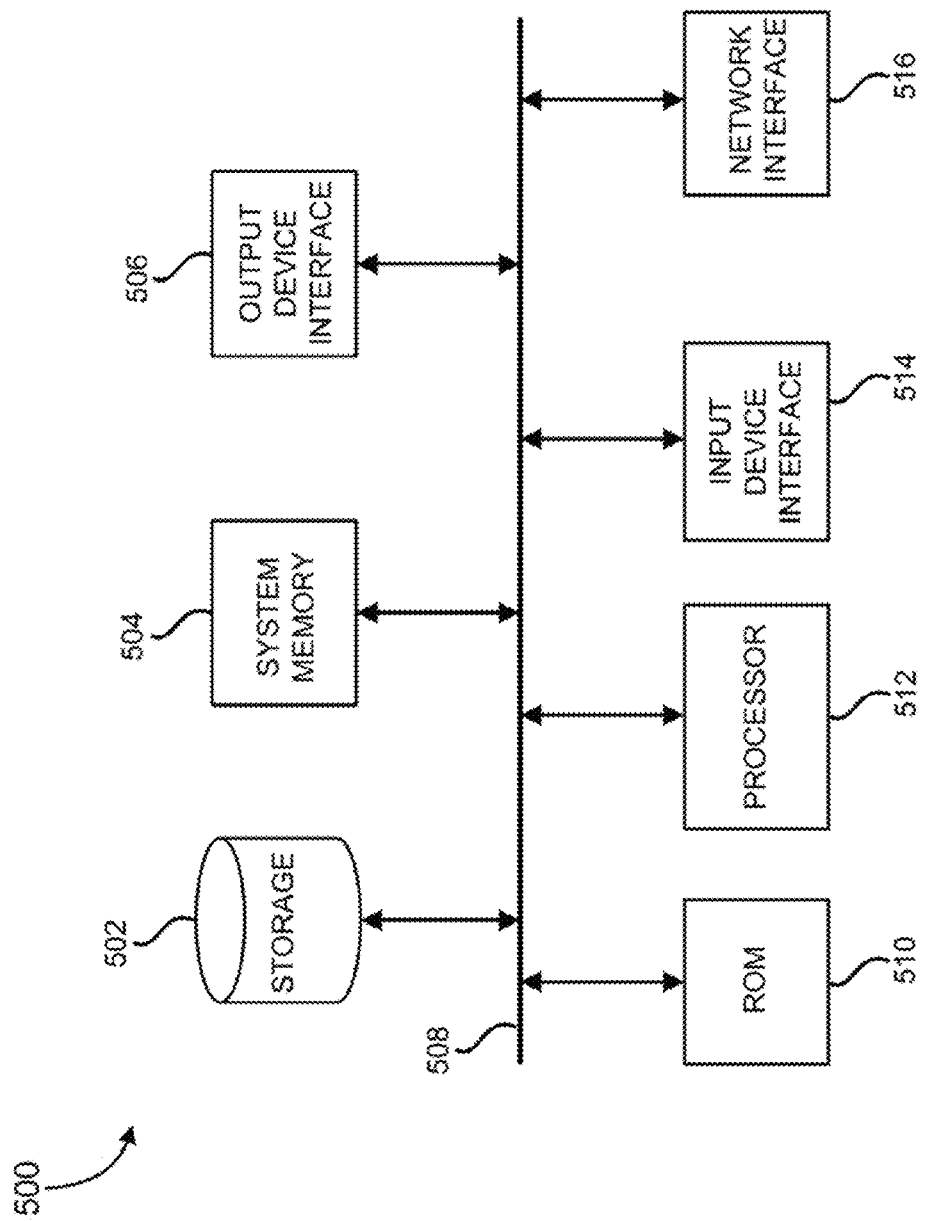
FIG. 5 conceptually illustrates an electronic system with which some aspects of the subject technology can be implemented.

FIG. 5 conceptually illustrates electronic system 500 with which implementations of the subject technology can be implemented. Electronic system 500, for example, can be, or can include, any of the control panel 1, the central control unit 2, a server, a desktop computer, a laptop computer, a tablet computer, a base station, or generally any electronic device. Such an electronic system includes various types of computer readable media and interfaces for various other types of computer readable media. Electronic system 500 includes bus 508, processing unit(s) 512, system memory 504, read-only memory (ROM) 510, permanent storage device 502, input device interface 514, output device interface 506, and network interface 516, or subsets and variations thereof.

Bus 508 collectively represents system, peripheral, and chipset buses that communicatively connect the numerous internal devices of electronic system 500. In one or more implementations, bus 508 communicatively connects processing unit(s) 512 with ROM 510, system memory 504, and permanent storage device 502. From these various memory units, processing unit(s) 512 retrieves instructions to execute and data to process in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. One or more implementations of the subject disclosure use a mass-storage device (such as a magnetic or optical disk and its corresponding disk drive) as permanent storage device 502.

Other implementations use a removable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such as random access memory. System memory 504 stores any of the instructions and data that processing unit(s) 512 needs at runtime. In one or more implementations, the processes of the subject disclosure are stored in system memory 504, permanent storage device 502, and/or ROM 510. From these various memory units, procession unit(s) 512 retrieves instructions to execute and data to process in order to execute the processes of one or more implementations.

Bus 508 also connects to input and output device interfaces 514 and 506. Input device interface 514 enables a user to communicate information and select commands to the electronic system. Input devices used with input device interface 514 include, for example, alphanumeric keyboards and pointing devices (also called "cursor control devices", touchpads, trackpads, or generally any device capable of receiving user input. Output device interface 506 enables, for example, the display of images generated by electronic system 500. Output devices used with output device interface 506 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more implementations may include devices that function as both input and output devices, such as a touchscreen. In these implementations, feedback provided to the user can be any form of sensory feedback, such as visual feedback, auditory feedback, or tactile feedback; and input from the user can be received in any form, including acoustic, speech, or tactile input.

Finally, as shown in FIG. 5, bus 508 also couples electronic system 500 to a network (not shown) through network interface 516. In this manner, the computer can be a part of a network of computers (such as a local area network ("LAN"), a wide area network ("WAN"), or an Intranet, or a network of networks, such as the Internet. Electronic system 500 may retrieve and/or receive information, e.g. via the network interface 516, from a cloud system, e.g. a cloud storage system. Any or all components of electronic system 500 can be used in conjunction with the subject disclosure.

In one or more implementations, the denominator and numerator of any ratio may be swapped, e.g. the ratio of two areas may be determined by dividing the first area by the second area or the second area by the first area. However, if the denominator and numerator of a ratio are swapped, the value of a threshold that the ratio is compared to may also be swapped accordingly.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more implementations, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more implementations, the computer readable media is non-transitory computer readable media, computer readable storage media, or non-transitory computer readable storage media.

In one or more implementations, a computer program product (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more implementations are performed by one or more integrated circuits, such as application specific integrated circuits (ASICs) or field programmable gate arrays (FPGAs). In one or more implementations, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used in this specification and any clauses of this application, the terms "computer", "server", "processor", and "memory" all refer to electronic or other technological devices. These terms exclude people or groups of people. For the purposes of the specification, the terms "display" or "displaying" means displaying on an electronic device.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. §101, 102, or 103, nor should they be interpreted in such a way.

What is claimed is:

1. A lung ventilation apparatus comprising:
a control panel, and
a graphical user interface associated with the control panel, the graphical user interface comprising a central strip content item covering at least 50% of a total area of the graphical user interface, the central strip content item representing at least one of a patient monitoring screen or surveillance screen, the central strip content item comprising a first portion and a second portion,
wherein the first portion comprises numerical elements indicating ventilation parameters of a patient, and the second portion comprises a graphical element indicating pressure at a patient airway,
wherein the graphical element that indicates pressure at the patient airway is a floating element that is configured to move proportionally to the pressure in a vertical way in real-time to display a real-time pressure level, in relation to a mark that indicates a Continuous Positive Airway Pressure (CPAP) adjusted level, and wherein the floating element is a circle and the mark includes two arrows pointing inward and facing each other.

2. The lung ventilation apparatus according to claim 1, wherein the central strip content item covers 80% or more of the total area of the graphical user interface.

3. The lung ventilation apparatus according to claim 1, wherein the second portion comprises two line marks showing pressure scale for minimum and maximum pressure fluctuation.

4. The lung ventilation apparatus according to claim 3, wherein the pressure scale automatically changes to accommodate mandatory cycles.

5. The lung ventilation apparatus according to claim 1, wherein the floating element comprises a color that indicates when a respiration cycle is in an inhalation or exhalation phase.

6. The lung ventilation apparatus according to claim 5, wherein the first portion presents numerical elements related to $FiO_2$, CPAP, and Respiratory Rate.

7. The lung ventilation apparatus according to claim 5, wherein the graphical user interface comprises a third portion presenting an iconic element that indicates occurrence of a respiratory cycle of the patient.

8. The lung ventilation apparatus according to claim 7, wherein the iconic element indicates a start, duration, and completion of an inspiratory phase, an exhalation phase, and a cycle type.

9. The lung ventilation apparatus according to claim 7, wherein the iconic element represents a figure of at least one of right and left lungs, a bronchial tree, a trachea, or a diaphragm of the patient.

10. The lung ventilation apparatus according to claim 9, wherein the iconic element represents the figure of the right and left lungs, and wherein a color code is used for the lungs to distinguish inspiration and exhalation of the patient.

11. The lung ventilation apparatus according to claim 7, wherein the first, second, and third portions are arranged in the central strip content item of the graphical user interface in a proportion of substantially ⅓ for each portion, the first portion being displayed at a right side of the patient monitoring screen, the second portion being displayed at a left side of the patient monitoring screen, and the third portion being displayed between the first portion and the second portion.

12. The lung ventilation apparatus according to claim 5, wherein the graphical user interface comprises a lower strip content item arranged to present alarm and control access menus arrayed in addition to fast access controls, the lower strip content item covering a portion equivalent to substantially 15% or more of the total graphical user interface area.

13. The lung ventilation apparatus according to claim 5, wherein the graphical user interface comprises an upper strip content item arranged to present general information including at least one of a date, hour, or patient type, in addition to a middle section configured to provide a visual alarm indicator, the upper strip content item covering a portion including an area equivalent to substantially 5% or more of the total graphical user interface area.

14. A system for lung ventilation, the system comprising:
a graphical user interface;
one or more processors; and
a memory including instructions that, when executed by the one or more processors, cause the one or more processors to:
generate, on the graphical user interface, a central strip content item covering at least 50% of a total area of the graphical user interface, the central strip content item representing at least one of a patient monitoring screen or surveillance screen, the central strip content item comprising a first portion and a second portion,
wherein the first portion comprises numerical elements indicating ventilation parameters of a patient, and the second portion comprises a graphical element indicating pressure at a patient airway,
wherein the graphical element that indicates pressure at the patient airway is a rotating element that is configured to rotate proportionally to the pressure in real-time to display a real-time pressure level, in relation to a scale that indicates a Continuous Positive Airway Pressure (CPAP) adjusted level, and
wherein the rotating element is a pointer.

15. The system for lung ventilation according to claim 14, wherein the rotating element is a pointer that is configured to move in relation to a semi-circular scale including CPAP adjusted level at a middle position.

16. The system for lung ventilation according to claim 15, wherein the second portion comprises two line marks showing pressure scale for minimum and maximum pressure fluctuation.

17. The system for lung ventilation according to claim 16, wherein the pressure scale automatically changes to accommodate mandatory cycles.

18. The system for lung ventilation according to claim 14, wherein the rotating element comprises a color that indicates when the respiration cycle is in an inhalation or exhalation phase.

19. A machine-readable medium comprising instructions stored therein, which when executed by a machine, cause the machine to perform operations, the machine-readable medium comprising:
instructions for generating; on a graphical user interface, a central strip content item covering at least 50% of a total area of the graphical user interface, the central strip content item representing at least one of a patient monitoring screen or surveillance screen; the central strip content item comprising a first portion and a second portion,
wherein the first portion comprises numerical elements indicating ventilation parameters of a patient, and the second portion comprises a graphical element indicating pressure at a patient airway,
wherein the graphical element that indicates pressure at the patient airway is a floating element that is configured to move proportionally to the pressure in a vertical way in real-time to display a real-time pressure level, in relation to a mark that indicates a Continuous Positive Airway Pressure (CPAP) adjusted level, and
wherein the floating element is a circle and the mark includes two arrows pointing inward and facing each other.

* * * * *